United States Patent [19]

Kurashina et al.

[11] Patent Number: 4,904,657

[45] Date of Patent: Feb. 27, 1990

[54] 4H-QUINOLIZIN-4-ONE COMPOUNDS EXHIBITING THERAPEUTIC ACTIVITIES

[75] Inventors: Yoshikazu Kurashina; Hiroshi Miyata; Den-ichi Momose, all of Matsumoto, Japan

[73] Assignee: Kissei Pharmaceutical Co., Ltd., Japan

[21] Appl. No.: 244,269

[22] Filed: Sep. 15, 1988

[30] Foreign Application Priority Data

Sep. 24, 1987 [JP] Japan .................. 62-239240
Dec. 4, 1987 [JP] Japan .................. 62-307090

[51] Int. Cl.[4] ........................... C07D 213/60
[52] U.S. Cl. ................. 514/233.2; 514/254; 514/306; 544/127; 544/362; 546/138
[58] Field of Search .............. 544/127, 362; 514/233.2, 254, 306; 546/138

[56] References Cited

U.S. PATENT DOCUMENTS 4,691,018 9/1987 Mori et al. ............... 546/309
4,698,349 10/1987 Kitaura et al. ............ 546/138

FOREIGN PATENT DOCUMENTS 62-00076 1/1987 Japan .
0277755 11/1987 Japan .................. 546/138

OTHER PUBLICATIONS

CA 70:106328y, Kobayashi et al., Synthesis of α-bis (methylthio)methylene-2 pyridine-acetonitriles, 1970, 89(2), pp. 203–208.
CA 76:85663k, Kobayashi et al., Quinolizine Derivatives, 1971, 91(12), pp. 1275–1278.
CA 72:100647n, Kobayashi et al., Reactions of 3-Cyano-4H-Quinolizin-4-ones, 1970, 90(2), pp. 127–131.
Dornow et al., "Methoxy-Methylen-Malonitrile Amine", Chemische Berichte, vol. 91, pp. 1830–1834, 1958.
Gompper et al., "Dithiocarbonic Acid and Ketenmercaptan", Chemische Berichte, vol. 95, pp. 2861–2870, 1962.
Okudaira et al., "Reaginic Antibody Formation in Mouse", Cellular Immunology, vol. 58, pp. 188–201, 1981.
Vaz et al., "Persistent Formation of Reagins", Immunology, vol. 21, 99. 11–12, 1971.
Coca & Grove, "Studies in Hypersensitiveness", J. Immunol., vol. 10, pp. 445–465, 1925.
Ishizaka et al., "Physico-Chemical Properties of Human Reaginic Antibody", J. Immunol., vol. 97, No. 1, pp.75–85, 1966.
Haraguchi et al., "A Specific Inhibitor . . . Fructopyranoside", J. Med. Chem., vol. 25, No. 12, pp. 1495–1499, 1982.
Compendium of Organic Synthetic Methods, Ed. by I. T. Harrison, Wiley Interscience, New York, vol. 1, pp. 272–279.

Primary Examiner—Mary C. Lee
Assistant Examiner—Catherine S. Kilby Scalzo
Attorney, Agent, or Firm—Depaoli & O'Brien

[57] ABSTRACT

This invention provides novel 4H-quinolizin-4-one compounds which exhibit a selective inhibitory activity against IgE-antibody formation, and have utility for treatment of diseases associated with IgE formation in mammals, such as allergic bronchial asthma, allergic rhinitis, atopic dermatitis, hypersensitiveness, and the like.

4 Claims, No Drawings

4H-QUINOLIZIN-4-ONE COMPOUNDS EXHIBITING THERAPEUTIC ACTIVITIES

FIELD OF THE INVENTION

This invention relates to novel quinolizinone derivatives having utility as therapeutic agents. More particularly this invention provides 4H-quinolizin-4-one components which exhibit selective inhibitory activities relative to IgE-antibody formation, and which have properties suitable for application as drugs for diseases associated with IgE such as allergic bronchial asthma, allergic rhinitis, atopic dermatitis, hypersensitiveness and the like.

BACKGROUND OF THE INVENTION

Several classes of immunoglobulin(s) [hereinafter referred to as Ig(s)] are well known as antibodies concerned with immune response. Most of Igs, especially immunoglobulin G (hereinafter referred to as IgG) which is one class of Igs, play an important role in self-defense mechanisms in mammals against foreign substances such as viruses, bacteria, tumours and the like.

However, immunoglobulin E (hereinafter referred to as IgE) which is another class of Igs, has been confirmed to be primarily responsible for diseases such as allergic bronchial asthma, allergic rhinitis, atopic dermatitis, hypersensitiveness, and the like (Journal of Immunology, Vol. 10, p 445. 1925, Journal of Immunology, Vol. 97, p 75, 1966). It also has been confirmed that serum concentrations of IgE in most allergic patients suffering from those diseases are higher in general than those in normal ones.

Therefore, for a causal and useful treatment of such diseases associated with IgE, selective inhibitors of IgE formation are being actively sought. The prospective inhibitors preferably would not inhibit excessively any class of Igs except IgE for reasons mentioned above.

Up to the present time, various compounds have been reported to inhibit IgE formation in literature such as [Japanese patent application (OPI) No. 76/87 (the term "OPI" used herein refers to an unexamined Japanese patent application); U.S. Pat. Nos. 4,395,405 and 4,691,018; British patent application No. 2,020,665(A); J. Med. Chem. Vol. 25, No. 12, pages 1495-1499, 1982].

Of particular interest with respect to the present invention are publications which disclose compounds having a substituted 4H-quinolizin-4-one nucleus.

Process embodiment for production of 1-, 2- and 3-substituted 4-quinolizin-4-one derivatives are described in Yakugaku Zasshi, Vol. 89, No. 2, pages 203-208, 1969, ibid. Vol. 90, No. 2, pages 127-131, 1970, ibid. Vol. 91, No. 12, pages 1275-1278, 1971, ibid. Vol. 94, No. 1, pages 44-49, 1974, 1977, Chem. Pharm. Bull. Vol. 18, No. 1, pages 124-127, 1970, ibid. Vol. 21, No. 5, pages 921-925, 1973, J. Heterocycl. Chem., Vol. 10, No. 2, pages 139-142, 1973, J. Chem. Soc. (c), pages 1143-1146, 1969, Monatish. Chem., Vol 114, pages 485-493, 1983.

Anti-tumor activity of 1-, 2-, and 3-substituted 4H-quinolizin-4-one derivatives of formula:

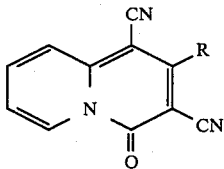

where R is methylthio, piperidino, N,N-diethyl aminoethylamino and benzylamino is disclosed in Yakugaku Zasshi, Vol 97, No. 9, pages 1039-1045, 1988.

European patent application 157346(A2) and Japanese patent application (OPI) No. 222482/85 which are counterparts of British patent application Nos. 8408292 and 8429710, filed Mar. 30, 1984 and Nov. 23, 1984, respectively, disclose quinolizinone derivatives having an inhibitory activity on allergies and ulcers, which derivatives correspond to the formula:

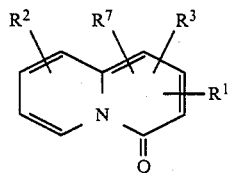

where $R^1$ is carboxy, amidated carboxy, cyano, thiocarbamoyl or tetrazolyl; $R^7$ is hydrogen or aryl; $R^2$ is hydrogen, hydroxy, lower alkyl or lower alkoxy; $R^3$ is hydrogen, hydroxy, lower alkyl, lower alkoxy, lower alkenyloxy, aryl which may have suitable substituents, arylthio, aroyl, ar(lower)alkyl, arenesulfonyl, arylamino which may have a suitable substituent or aryloxy; and $R^2$ and $R^3$ can be located at any place on the quinolizine ring and can be linked together to form —CH$_2$CH$_2$CH$_2$—, —CH═CH— or —CH═CH—CH═C—; and pharmaceutically acceptable salts thereof.

Japanese patent application (OPI) No. 77385/87 which is a counterpart of U.S. patent application Ser. No. 770953 filed Aug. 30, 1985, discloses quinolizinone derivatives having inhibitory activity on allergies and ulcers, which derivatives correspond to the formula:

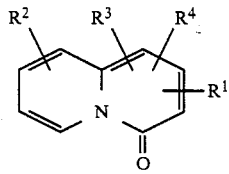

where $R^1$ is carboxy, tetrazolylcarbamoyl or amino-substituted triazolylcarbamoyl; $R^2$ is hydrogen or lower alkoxy; $R^3$ is hydrogen, aroyl, aryl, carboxy or protected carboxy; $R^4$ is hydrogen or hydroxy; with the proviso that (i) when $R^3$ is hydrogen, $R^4$ is hydroxy, (ii) when $R^3$ is aryl, $R^1$ is amino-substituted triazolylcarbamoyl and (iii) when $R^3$ is aroyl, $R^2$ is lower alkoxy; and pharmaceutically acceptable salts thereof.

U.S. Pat. No. 4,650,804 which is a counterpart of British patent application Nos. 8408292 and 829710, filed Mar. 30, 1984 and Nov. 23, 1984, respectively, disclose quinolizinone derivatives having inhibitory activity on allergies and ulcers, which derivatives correspond to the formula:

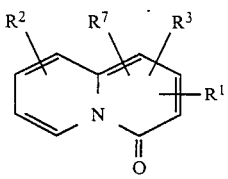

where $R^1$ is tetrazolylcarbamoyl; $R^7$ is hydrogen or aryl selected from phenyl, tolyl, xylyl, cumenyl, naphthyl and biphenylyl; $R^2$ is hydrogen, hydroxy, lower alkyl or lower alkoxy; $R^3$ is hydrogen, hydroxy, lower alkyl, lower alkoxy, lower alkenyloxy, phenyl, naphthyl, biphenylyl, phenyl having one or more substituents selected from halogen, lower alkyl and lower alkoxy, arylthio selected from phenylthio, tolylthio, xylylthio, cumenylthio, naphthylthio and biphenylylthio, aroyl selected from benzoyl, toluoyl and naphthoyl ar(-lower)-alkyl selected from phenyl(-lower)alkyl, tolyl(-lower)-alkyl, xylyl(lower)alkyl, cumenyl(lower)alkyl, naphthyl-(lower)alkyl and biphenylyl(lower)alkyl, arenesulfonyl selected from benzenesulfonyl and p-toluenesulfonyl, arylamino selected form phenylamino, naphthylamino, biphenylylamino, phenylamino having lower alkyl on the nitrogen atom or aryloxy selected from phenoxy and tolyloxy; or pharmaceutically acceptable salts thereof.

U.S. Pat. No. 4,698,349 filed Aug.30, 1985, disclose quinolizinone derivatives having inhibitory activity on allergies and ulcers, which derivatives correspond to the formula:

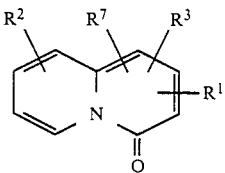

where $R^1$ is carboxy, carbamoyl, phenylcarbamoyl which may have hydroxy, cyano or thiocarbamoyl; $R^7$ is hydrogen or aryl selected from phenyl, tolyl, xylyl, cumenyl, naphthyl and biphenylyl; $R^2$ is hydrogen, hydroxy, lower alkyl or lower alkoxy; $R^3$ is hydrogen, hydroxy, lower alkyl, lower alkoxy, lower alkenyloxy, phenyl, naphthyl, biphenylyl, phenyl having one or more substituents selected from halogen, lower alkyl and lower alkoxy, arylthio selected from phenylthio, tolylthio, xylylthio, cumenylthio, naphthylthio and biphenylylthio, aroyl selected from benzoyl, toluoyl and naphthoyl ar(lower)-alkyl selected from phenyl(-lower)alkyl, tolyl(lower)alkyl, xylyl(lower)alkyl, cumenyl(lower)alkyl, naphthyl(lower)alkyl and biphenylyl(-lower)alkyl, arenesulfonyl selected from benzenesulfonyl and p-toluenesulfonyl, arylamino selected from phenylamino, naphthylamino, biphenylylamino, phenylamino having lower alkyl on the nitrogen atom or aryloxy selected from phenoxy and tolyloxy; or pharmaceutically acceptable salts thereof.

In none of the publications described above is there any disclosure or suggestion that novel substituted 4H-quinolizin-4-one of the type provided with the present invention might exhibit an inhibitory activity against IgE formation in mammals.

As an invention related to the present invention, the present inventors have been filed U.S. patent application Ser. No. 147,549, on Jan. 25, 1988.

SUMMARY OF THE INVENTION

Accordingly, an object of this invention is to provide novel quinolizinone derivatives which exhibit selective inhibitory activities against IgE formation when administered to human or to other mammals.

Another object of this invention is to provide pharmaceutical compositions comprising quinolizinone derivatives.

A further object of this invention is to provide methods for treatment of diseases associated with IgE formation, such as allergic bronchial asthma, allergic rhinitis, atopic dermatitis, hypersensitiveness, and the like.

Other object, features and advantages of this invention will be apparent from the following description of the invention.

The present invention provides novel 4H-quinolizin-4-one derivatives represented by the formula:

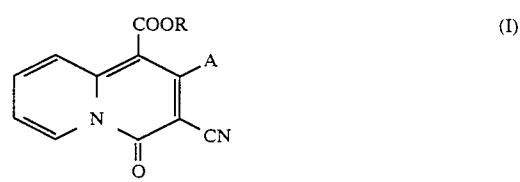

where R is an alkyl group or a phenylalkyl group; A is a substituted or unsubstituted phenyl group or a substituted or unsubstituted 5 or 6 membered heterocyclic group; with the proviso that the heterocyclic group is bonded to the quinolizine ring at a nitrogen atom of the heterocyclic ring.

In the above and subsequent description of the present specification, the terms used in the definitions of the symbols have the following meanings.

The term "alkyl" and the "alkyl" moiety in "phenylalkyl", "hydroxyalkyl", "alkylthio" and "morpholinocarbonylalkyl" refer to a straight or branched alkyl group having 1 to 6 carbon atoms.

The term "alkoxy" refers to a straight or branched alkoxy group having 1 to 6 carbon atoms.

The term "acyl" refers to an aliphatic acyl group such as acetyl, propionyl and cyclohexylacetyl, an aromatic acyl group such as benzoyl which may have suitable substituents on the ring, and an aromatic aliphatic acyl group such as phenylacetyl and phenylpropionyl which may have suitable substituents on the ring and/or chain. An acyl group has a content of 2 to 12 carbon atoms.

The term "a substituted or unsubstituted phenyl group" refers to a substituted or unsubstituted phenyl group with a content of 6 to 24 carbon atoms, which may have 1 to 3 substituents selected from a halogen atom, an alkyl group, an alkoxy group, hydroxy group, nitro group, amino group, an acylamino group, an alkylthio group, phenyl group, benzoyl group, benzyloxy group and methylenedioxy group on the ring; with the proviso that when substituents are 2 or 3, they may be the same or different.

The term "a 5 or 6 membered heterocyclic group" refer to a saturated or unsaturated 5 or 6 membered heterocyclic group which may contain one or more hetero atoms in addition to a nitrogen atom which is bonded to the quinolizine ring, such as 1-pyrrolidinyl, piperidino, morpholino, 1-piperazinyl, 1-imidazolyl and 1-triazolyl group.

Substituent attached to the 5 or 6 membered heterocyclic group defined above is a group selected from an alkyl group, phenyl group, a phenylalkyl group, a hydroxyalkyl group, a morpholinocarbonylalkyl group and formyl group.

In another embodiment this invention provides a 4H-quinolizin-4-one compound corresponding to the formula:

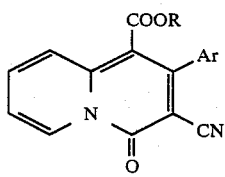

(Ia)

where R is an alkyl group or a phenylalkyl group; Ar is a substituted or unsubstituted phenyl group.

In another embodiment this invention provides a 4H-quinolizin-4-one compound corresponding to the formula:

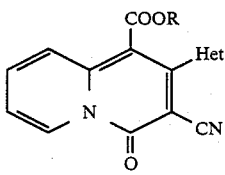

(Ib)

where R is an alkyl group or a phenylalkyl group; Het is a 5 or 6 membered heterocyclic group; with the proviso that the heterocyclic group is bonded to the quinolizine ring at a nitrogen atom of the heterocyclic ring.

DETAILED DESCRIPTION OF THE INVENTION

The 4H-quinolizin-4-one derivatives of the present invention selectively inhibit the formation of IgE.

Pharmacological test data indicated that the 4H-quinolizin-4-one derivatives of formula (I) of the present invention have potential utility as drugs for diseases associated with IgE, such as allergic bronchial asthma, allergic rhinitis, atopic dermatitis, hypersensitiveness, and the like.

The 4H-quinolizin-4-one compounds of formula (I) of the present invention can be prepared as follows:

For example, of the 4H-quinolizin-4-one derivatives of formula (I), the 4H-quinolizin-4-one compounds corresponding to the formula (Ia):

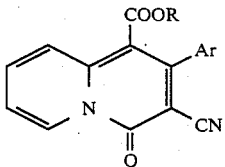

(Ia)

where R, Ar and n are as previously defined, can be prepared by the reaction of a compound corresponding to the formula:

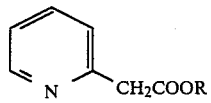

(II)

where R is as previously defined, with a compound corresponding to the formula:

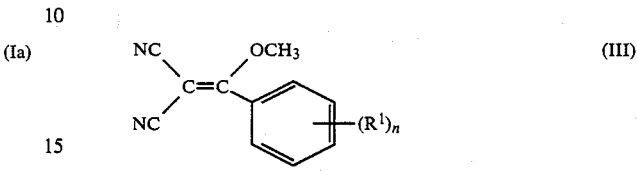

(III)

where $R^1$ is a group selected from a halogen atom, an alkyl group, an alkoxy group, an acyloxy group, nitro group, an acylamino group, an alkylthio group, phenyl group, benzoyl group, benzyloxy group and methylenedioxy group; n is zero or an integer of 1-3; with the proviso that when n is 2 or 3, $R^1$ may be same or different, to prepare a compound corresponding to the formula:

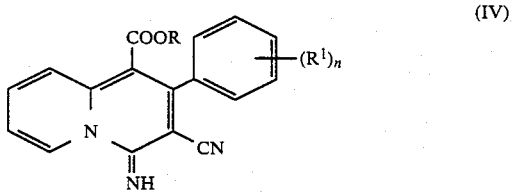

(IV)

where R, $R^1$ and n are previously defined, and then by hydrolyzing the compound of formula (IV) above obtained under acidic conditions, and if necessary, by deacylating or reducing the obtained products.

Of the 4H-quinolizin-4-one derivatives of formula (I) of the present invention, the 4H-quinolizin-4-one compounds corresponding to formula (Ib) can be prepared according to the method described by Kobayashi et al. in Yakugaku Zasshi Vol. 89, No. 2, pp 203-208, 1969. That is a 4H-quinolizin-4-one derivative of the present invention corresponding to the formula:

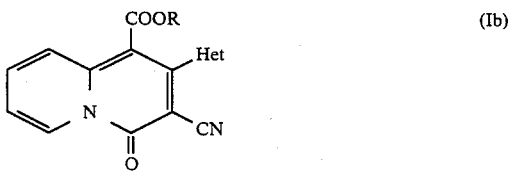

(Ib)

where R and Het are as previously defined, can be prepared by the reaction of a compound corresponding to the formula:

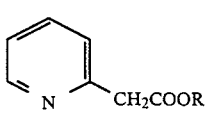

(II)

where R is as previously defined, with a compound corresponding to the formula:

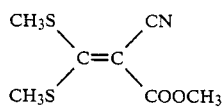

to prepare a compound corresponding to the formula:

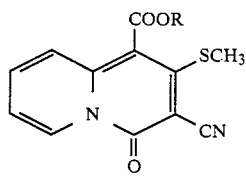

where R is as previously defined, followed by the reaction of the compound of formula (VI) above obtained with a heterocyclic compound corresponding to the formula:

H—Het     (VII)

where Het is as previously defined.

Compounds of formulae (II), (III) and (V) for use as starting materials can be prepared as follows:

A compound of formula (II) can be prepared from 2-pyridylacetic acid according to the manner described in Compendium of Organic Synthetic Methods, Ed. by I. T. Harrison and S. Harrison, Wiley-Interscience New York, Vol. 1, pp 272–279 (1971).

A compound of formula (III) can be prepared by the reaction of malononitrile, a substituted or unsubstituted benzoyl chloride and dimethyl sulfate in accordance with a procedure described in Chemische Berichte, Vol 91, pp 1830–1834, 1958.

A compound of formula (V) can be prepared by the reaction of methyl cyanoacetate, carbon disulfide and a dimethyl sulfate in accordance with a procedure described in Chemische Berichte, Vol. 95, pp 2861–2870, 1962.

The reaction of a compound of formula (II) with a compound of formula (III) can be conducted preferably in accordance with the following method.

A compound of formula (II) is reacted with a compound of formula (III) in equal molar quantities, in the presence of a base such as sodium hydride or sodium alkoxide in inert organic solvent. And the reaction mixture is worked up to conventional procedures to obtain a 4-imino compound of formula (IV). And then, the compound of formula (IV) above obtained is hydrolyzed under acidic conditions to obtain the 4H-quinolizin-4-one compound of formula (Ia).

The reaction of a compound of formula (II) with a compound of formula (V) can be conducted in accordance with the following preferred method.

A mixture of a compound of formula (II) and a compound of formula (V) in equal molar quantities is heated at 100°–120° C. for 2–10 hours, in the presence or absence of organic solvent, and then the reaction mixture is worked up to conventional procedures to obtain a compound of formula (VI).

And then the compound of formula (VI) above obtained is reacted with a compound of formula (VII) in equal molar or excess quantities at a temperature between room temperature to 140° C. for 2–48 hours, in the presence or absence of organic solvent, and the reaction mixture is worked up to conventional procedures to obtain the 4H-quinolizin-4-one compound of formula (Ib).

The 4H-quinolizin-4-one derivatives represented by formula (I) of the present invention exhibit selective inhibitory activities on IgE formation. The inhibitory activities of the quinolizinone derivatives of formula (I) are confirmed by the determination of Igs produced in cultures of spleen cells from BALB/c mice which exhibit an adoptive secondary immune response against dinitrophenylated proteins of ascaris (DNP-As) according to a procedure described in Cellular Immunology, Vol. 58, pp 188–201, 1981. And the inhibitory activities of the quinolizinone derivative of formula (I) also are confirmed by the determination of serum concentrations of Igs in BALB/c mice which are immunized by DNP-As according to a procedure described in Immunology, Vol 21, pp 11–12, 1971.

The results obtained by these tests demonstrate that the compounds of formula (I) of the present invention inhibit IgE formation, and minimally affect the production of Igs other than IgE.

From the results obtained by these pharmacological tests, it can be expected that the compound of formula (I) of the present invention has properties suitable for application as a therapeutic agent for treatment of diseases associated with IgE in mammals.

Furthermore, the compounds of the formula (I) of the present invention also selectively inhibit IgE production in cultures of peripheral blood lymphocytes from atopic patients.

An acute toxicological test in mice shows that the compounds of formula (I) of the present invention have very low acute toxicity.

The 4H-quinolizin-4-one derivatives of the general formula (I) of the present invention can be administered in various dosage forms depending upon the intended therapy. Typical dosage forms which can be used are tablets, pills, powder, liquid preparations, suspensions, emulsions, granules, capsules, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc; binders such as gum arabic powder, tragacanth powder, and ethanol; and disintegrants such as laminaria and agar. The tablets, if desired, can be coated and made into sugar-coated tablets, gelatin-coated tablets, film-coated tablets, or tablets coated with two or more layers.

When a pharmaceutical composition is formulated into an injectable preparation, it is preferred that the resulting injectable solution and suspension are sterilized and rendered isotonic with respect to blood. In making the pharmaceutical composition into a solution or suspension, any diluents customarily used in the art can be employed. Examples of suitable diluents include water, ethyl alcohol, propylene glycol, polyoxyethylene sorbitol, and sorbitan esters. Sodium chloride, glucose or glycerol may be incorporated into a therapeutic agent in an amount sufficient to prepare an isotonic solution. The therapeutic agent may further contain ordinary dissolving aids, buffers, pain-alleviating agents, and preservatives, and optionally, coloring agents, fragrances, flavors, sweeteners, and other pharmaceutically active agents.

The dosage of the quinolizinone derivatives of the present invention may be in a range between approximately 0.1 mg to 10 mg per kg of mammal weight by an oral administration, or between about 0.02 mg to 5 mg per kg of mammal weight by a parenteral administration per day in multiple doses depending upon the type of mammal disease, the severity of condition to be treated, and the like.

In another embodiment this invention provides a method for the treatment of diseases associated with IgE-antibody formation in a mammal which comprises administering an effective dosage of an IgE-formation-inhibiting 4H-quinolizin-4-one compound to the mammal.

In a further embodiment this invention provides a pharmaceutical composition for the treatment of diseases associated with IgE-antibody formation in a mammal, which composition contains an effective dosage of an IgE-formation-inhibiting 4H-quinolizin-4-one compound.

This invention is further illustrated in more detail by way of the following examples and pharmacological data.

EXAMPLE 1

3-Cyano-1-ethoxycarbonyl-2-phenyl-4H-quinolizin-4-one (S-1)

A mixture of 2.50 g of ethyl 2-pyridylacetate and 2.79 g of 2-cyano-3-methoxy-3-phenylacrylonitrile was dissolved in 15 ml of dry N,N-dimethylformamide. To the solution was added 0.61 g of 60% sodium hydride and the reaction mixture was stirred for 1 hour at 60° C. The reaction mixture was poured into ice-water, and precipitated crystals were collected by filtration, washed with water and dried under vacuum to obtain 2.50 g of 3-cyano-1-ethoxycarbonyl-4-imino-2-phenyl-4H-quinolizine.

The imino compound obtained was dissolved in 50 ml of 90% acetic acid and the reaction mixture was heated under reflux for 72 hours. After completion of the reaction, the solvent was evaporated under reduced pressure. The residue was dissolved in dichloromethane and the solution was washed successively with 1N-hydrochloric acid, water and saturated sodium chloride solution and dried over anhydrous sodium sulfate. The solvent was evaporated under reduced pressure and the residue was recrystallized from methanol to obtain 2.13 g of 3-cyano-1-ethoxycarbonyl-2-phenyl-4H-quinolizin-4-one.

Melting point: 175°–176° C.
IR (KBr): 2210, 1715, 1665, 1625, 1600 cm$^{-1}$.
$^1$H NMR (CDCl$_3$): δ 0.77(t, 3H), 3.92(q, 2H), 7.36–7.52(m, 6H), 7.84(dt, 1H), 8.23(d, 1H), 9.39(d, 1H).

| Elementary analysis: C$_{19}$H$_{14}$N$_2$O$_3$ | | | |
|---|---|---|---|
| | C % | H % | N % |
| Calcd. | 71.69 | 4.43 | 8.80 |
| Found | 71.69 | 4.43 | 8.81 |

EXAMPLE 2

The following compounds were obtained according to the same procedure as described in Example 1.

2-(4-Biphenyl)-3-cyano-1-ethoxycarbonyl-4H-quinolizin-4-one (S-2)

Melting point: 216°–221° C.
IR (KBr): 2220, 1710, 1670, 1625 cm$^{-1}$.
$^1$H NMR (CDCl$_3$): δ 0.77(t, 3H), 3.96(q, 2H), 7.36–7.78(m, 10H), 7.85(dt, 1H), 8.25(d, 1H), 9.40(d, 1H).

| Elementary analysis: C$_{25}$H$_{18}$N$_2$O$_3$ | | | |
|---|---|---|---|
| | C % | H % | N % |
| Calcd. | 76.13 | 4.60 | 7.10 |
| Found | 76.41 | 4.48 | 7.19 |

2-(4-Bromophenyl)-3-cyano-ethoxycarbonyl-4H-quinolizin-4-one (S-3)

Melting point: 233°–236° C.
IR (KBr): 2220, 1710, 1680, 1625 cm$^{-1}$.
$^1$H NMR (CDCl$_3$): δ 0.86(t, 3H), 3.99(q, 2H), 7.30(d, 2H), 7.42(t, 1H), 7.64(d, 2H), 7.86(dt, 1H), 8.26(d, 1H), 9.40(d, 1H).

| Elementary analysis: C$_{19}$H$_{13}$N$_2$O$_3$Br | | | |
|---|---|---|---|
| | C % | H % | N % |
| Calcd. | 57.45 | 3.30 | 7.05 |
| Found | 57.64 | 3.15 | 7.20 |

3-Cyano-1-ethoxycarbonyl-2-(4-tert-butylphenyl)-4H-quinolizin-4-one (S-4)

Melting point: 195°–198° C.
IR (KBr): 2225, 1715, 1680, 1625 cm$^{-1}$.
$^1$H NMR (CDCl$_3$): δ 0.70(t, 3H), 1.35(s, 9H), 3.92(q, 2H), 7.37(d, 3H), 7.50(d, 2H), 7.83(dt, 1H), 8.21(d, 1H), 9.38(d, 1H).

| Elementary analysis: C$_{23}$H$_{22}$N$_2$O$_3$ | | | |
|---|---|---|---|
| | C % | H % | N % |
| Calcd. | 73.78 | 5.92 | 7.48 |
| Found | 73.95 | 5.99 | 7.66 |

3-Cyano-2-(3,4-dimethoxyphenyl)-1-ethoxycarbonyl-4H-quinolizin-4-one (S-5)

Melting point: 163°–164° C.
IR (KBr): 2215, 1715, 1665, 1625 cm$^{-1}$.
$^1$H NMR (CDCl$_3$): δ 0.88(t, 3H), 3.91(s, 3H), 3.95(s, 3H), 4.00(q, 2H), 6.95–7.07(m, 3H), 7.37(t, 1H), 7.82(dt, 1H), 8.16(d, 1H), 9.37(d, 1H).

| Elementary analysis: C$_{21}$H$_{18}$N$_2$O$_5$ | | | |
|---|---|---|---|
| | C % | H % | N % |
| Calcd. | 66.66 | 4.80 | 7.40 |
| Found | 66.08 | 4.71 | 7.59 |

3-Cyano-1-ethoxycarbonyl-2-(4-methoxyphenyl)-4-quinolizin-4-one (S-6)

Melting point: 192°–195° C.
IR (KBr): 2220, 1715, 1680, 1625, 1610 cm$^{-1}$.
$^1$H NMR (CDCl$_3$): δ 0.86(t, 3H), 3.87(s, 3H), 3.99(q, 2H), 7.01(d, 2H), 7.35(d, 1H), 7.38(d, 2H), 7.81(dt, 1H), 8.16(d, 1H), 9.37(d, 1H).

| Elementary analysis: $C_{20}H_{16}N_2O_4$ | | | |
|---|---|---|---|
| | C % | H % | N % |
| Calcd. | 68.96 | 4.63 | 8.04 |
| Found | 68.25 | 4.56 | 7.91 |

3-Cyano-1-ethoxycarbonyl-2-(4-methylphenyl)-4H-quinolizin-4-one (S-7)

Melting point: 185.5°–186.5° C.
IR (KBr): 2220, 1700, 1675, 1625 cm$^{-1}$.
$^1$H NMR (CDCl$_3$): δ 0.80(t, 3H), 2.42(s, 3H), 3.96(q, 2H), 7.26–7.40(m, 5H), 7.82(dt, 1H), 8.19(d, 1H), 9.38(d, 1H).

| Elementary analysis: $C_{20}H_{16}N_2O_3$ | | | |
|---|---|---|---|
| | C % | H % | N % |
| Calcd. | 72.28 | 4.85 | 8.43 |
| Found | 72.30 | 4.79 | 8.41 |

3-Cyano-1-ethoxycarbonyl-2-(3,4-methylenedioxyphenyl)-4H-quinolizin-4-one (S-8)

Melting point: 216°–218° C.
IR (KBr): 2210, 1725, 1670, 1630 cm$^{-1}$.
$^1$H NMR (CDCl$_3$): δ 0.95(t, 3H), 4.04(q, 2H), 6.05(s, 2H), 6.88–6.92(m, 3H), 7.37(t, 1H), 7.83(dt, 1H), 8.16(d, 1H), 9.38(d, 1H).

| Elementary analysis: $C_{20}H_{14}N_2O_5$ | | | |
|---|---|---|---|
| | C % | H % | N % |
| Calcd. | 66.30 | 3.89 | 7.73 |
| Found | 66.60 | 3.76 | 7.78 |

3-Cyano-2-(2,4-dichlorophenyl)-1-ethoxycarbonyl-4H-quinolizin-4-one (S-9)

Melting point: 187°–188° C.
IR (KBr): 2210, 1720, 1680, 1625 cm$^{-1}$.
$^1$H NMR (CDCl$_3$): δ 0.90(t, 3H), 3.95–4.10(m, 2H), 7.21(d, 1H), 7.38(d, 1H), 7.47(t, 1H), 7.55(s, 1H), 7.91(dt, 1H), 8.53(d, 1H), 9.46(d, 1H).

| Elementary analysis: $C_{19}H_{12}N_2O_3Cl_2$ | | | |
|---|---|---|---|
| | C % | H% | N % |
| Calcd. | 58.93 | 3.12 | 7.23 |
| Found | 59.08 | 2.95 | 7.39 |

3-Cyano-2-phenyl-1-propoxycarbonyl-4H-quinolizin-4-one (S-10)

Melting point: 156°–158° C.
IR (KBr): 2210, 1700, 1670, 1620 cm$^{-1}$.
$^1$H NMR (CDCl$_3$): δ 0.64(t, 3H), 1.17(m, 2H), 3.82(t, 2H), 7.38(t, 1H), 7.40–7.51(m, 5H), 7.83(dt, 1H), 8.21(d, 1H), 9.40(d, 1H).

| Elementary analysis: $C_{20}H_{16}N_2O_3$ | | | |
|---|---|---|---|
| | C % | H % | N % |
| Calcd. | 72.28 | 4.85 | 8.43 |
| Found | 72.17 | 4.73 | 8.46 |

3-Cyano-1-methoxycarbonyl-2-phenyl-4H-quinolizin-4-one (S-11)

Melting point: 208°–211° C.
IR (KBr): 2220, 1715, 1675, 1625 cm$^{-1}$.
$^1$H NMR (CDCl$_3$): δ 3.43(s, 3H), 7.33–7.55(m, 6H), 7.84(dt, 1H), 8.19(d, 1H), 9.39(d, 1H).

| Elementary analysis: $C_{18}H_{12}N_2O_3$ | | | |
|---|---|---|---|
| | C % | H % | N % |
| Calcd. | 71.05 | 3.97 | 9.21 |
| Found | 71.02 | 3.87 | 9.21 |

3-Cyano-1-ethoxycarbonyl-2-(4-fluorophenyl)-4H-quinolizin-4-one (S-12)

Melting point: 209°–214° C.
IR (KBr): 2220, 1705, 1665, 1625 cm$^{-1}$.
$^1$H NMR (CDCl$_3$): δ 0.86(t, 3H), 3.98(q, 2H), 7.19(t, 2H), 7.36–7.46 (m, 3H), 7.86(dt, 1H), 8.23(d, 1H), 9.40(d, 1H).

| Elementary analysis: $C_{19}H_{13}N_2O_3F$ | | | |
|---|---|---|---|
| | C % | H % | N % |
| Calcd. | 67.85 | 3.90 | 8.33 |
| Found | 67.93 | 3.71 | 8.43 |

3-Cyano-1-ethoxycarbonyl-2-(3-fluoro-4-methylphenyl)-4H-quinolizin-4-one (S-13)

Melting point: 202°–203.5° C.
IR (KBr): 2220, 1725, 1675, 1620 cm$^{-1}$.
$^1$H NMR (CDCl$_3$): δ0.87(t, 3H), 2.33(brs, 3H), 4.00(q, 2H), 7.05–7.13(m, 2H), 7.30(t, 1H), 7.40(t, 1H), 7.85(dt, 1H), 8.22(d, 1H), 9.40(d, 1H)

| Elementary analysis: $C_{20}H_{15}N_2O_3F$ | | | |
|---|---|---|---|
| | C % | H % | N % |
| Calcd. | 68.57 | 4.32 | 8.00 |
| Found | 68.64 | 3.98 | 8.24 |

3-Cyano-2-(3,4-dimethylphenyl)-1-ethoxycarbonyl-4H-quinolizin-4-one (S-14)

Melting point: 160°–163° C.
IR (KBr): 2210, 1715, 1675, 1625 cm$^{-1}$.
$^1$H NMR (CDCl$_3$): δ 0.81(t, 3H), 2.31(brs, 6H), 3.97(q, 2H), 7.12–7.28(m, 3H), 7.36(t, 1H), 7.80(dt, 1H), 8.17(d, 1H), 9.37(d, 1H).

| Elementary analysis: $C_{21}H_{18}N_2O_3$ | | | |
|---|---|---|---|
| | C % | H % | N % |
| Calcd. | 72.82 | 5.24 | 8.09 |
| Found | 72.84 | 5.16 | 8.11 |

3-Cyano-1-ethoxycarbonyl-2-(4-ethoxyphenyl)-4H-quinolizin-4-one (S-15)

Melting point: 164°–166° C.
IR (KBr): 2210, 1705, 1675, 1625, 1605 cm$^{-1}$.
$^1$H NMR (CDCl$_3$): δ 0.87(t, 3H), 1.44(t, 3H), 3.99(q, 2H), 4.10(q, 2H), 6.99(d, 2H), 7.34(t, 1H), 7.37(d, 2H), 7.80(dt, 1), 8.16(dt, 1H), 9.37(d, 1H).

| Elementary analysis: $C_{21}H_{18}N_2O_4$ | | | |
|---|---|---|---|
| | C % | H % | N % |
| Calcd. | 69.60 | 5.01 | 7.73 |
| Found | 69.55 | 4.91 | 7.83 |

3-Cyano-1-ethoxycarbonyl-2-(4-isopropoxyphenyl)-4H-quinolizin-4-one (S-16)

Melting point: 168°–169° C.
IR (KBr): 2210, 1710, 1670, 1630, 1605 cm$^{-1}$.
$^1$H NMR (CDCl$_3$): δ 0.86(t, 3H), 1.38(d, 6H), 3.99(q, 2H), 4.63(m,1H), 6.98(d, 2H), 7.31–7.39(m, 3H), 7.80(dt, 1H), 8.17(d, 1H), 9.37(d, 1H).

| Elementary analysis: $C_{22}H_{20}N_2O_4$ | | | |
|---|---|---|---|
| | C % | H % | N % |
| Calcd. | 70.20 | 5.36 | 7.44 |
| Found | 69.77 | 5.20 | 7.55 |

3-Cyano-1-ethoxycarbonyl-2-(3-methoxyphenyl)-4H-quinolizin-4-one (S-17)

Melting point: 150.5°–151.5° C.
IR (KBr): 2220, 1710, 1670, 1620 cm$^{-1}$.
$^1$H NMR (CDCl$_3$): δ 0.83(t, 3H), 3.85(s, 3H), 3.97(q, 2H), 6.94–7.05 (m, 3H), 7.36–7.42(m, 2H), 7.84(dt, 1H), 8.22(d, 1H), 9.39(d, 1H).

| Elementary analysis: $C_{20}H_{16}N_2O_4$ | | | |
|---|---|---|---|
| | C % | H % | N % |
| Calcd. | 68.96 | 4.63 | 8.04 |
| Found | 68.97 | 4.46 | 7.97 |

2-(4-Benzyloxyphenyl)-3-cyano-1-ethoxycarbonyl-4H-quinolizin-4-one (S-18)

Melting point: 185°–187.5° C.
IR (KBr): 2220, 1705, 1670, 1625, 1610 cm$^{-1}$.
$^1$H NMR (CDCl$_3$): δ 0.83(t, 3H), 3.97(q, 2H), 5.13(s 2H), 7.08(d, 2H), 7.31–7.48(m, 8H), 7.81(dt, 1H), 8.17(d, 1H), 9.38(d, 1H).

| Elementary analysis: $C_{26}H_{20}N_2O_4$ | | | |
|---|---|---|---|
| | C % | H % | N % |
| Calcd. | 73.57 | 4.75 | 6.60 |
| Found | 73.64 | 4.60 | 6.62 |

3-Cyano-1-ethoxycarbonyl-2-(3,4,5-trimethoxyphenyl)-4H-quinolizin-4-one (S-19)

Melting point: 223.5°–225° C.
IR (KBr): 2220, 1720, 1680, 1630 cm$^{-1}$.
$^1$H NMR (CDCl$_3$): δ 0.89(t, 3H), 3.89(brs, 6H), 3.92(s, 3H), 4.00(q, 2H), 6.67(brs, 2), 7.38(t, 1H), 7.84(dt, 1H), 8.17(d, 1H), 9.38(d, 1H).

| Elementary analysis: $C_{22}H_{20}N_2O_6$ | | | |
|---|---|---|---|
| | C % | H % | N % |
| Calcd. | 64.70 | 4.94 | 6.86 |
| Found | 64.67 | 4.90 | 6.72 |

3-Cyano-1-ethoxycarbonyl-2-(4-nitrophenyl)-4H-quinolizin-4-one (S-20)

Melting point: 211°–214° C.
IR (KBr): 2210, 1710, 1680, 1625 cm$^{-1}$.
$^1$H NMR (CDCl$_3$): δ 0.83(t, 3H), 3.97(q, 2H), 7.48(t, 1H), 7.06(d, 2H), 7.93(dt, 1H), 8.38(m, 3H), 9.46(d, 1H).

| Elementary analysis: $C_{19}H_{13}N_3O_5$ | | | |
|---|---|---|---|
| | C % | H % | N % |
| Calcd. | 62.81 | 3.61 | 11.57 |
| Found | 62.23 | 3.43 | 11.12 |

3-Cyano-1-ethoxycarbonyl-2-(2-methoxyphenyl)-4H-quinolizin-4-one (S-21)

Melting point: 213.5°–214° C.
IR (KBr): 2220, 1715, 1680, 1625 cm$^{-1}$.
$^1$H NMR (CDCl$_3$): δ 0.80(t, 3H), 3.85(brs, 3H), 3.96(q, 2H), 7.00–7.10(m, 2 H), 7.20(d, 1H), 7.37(t, 1H), 7.44(t, 1H), 7.82(dt, 1H), 8.35(d, 1 H), 9.39(d, 1H).

| Elementary analysis: $C_{20}H_{16}N_2O_4$ | | | |
|---|---|---|---|
| | C % | H % | N % |
| Calcd. | 68.96 | 4.63 | 8.04 |
| Found | 68.72 | 4.40 | 8.15 |

2-(3-Bromophenyl)-3-cyano-1-ethoxycarbonyl-4H-quinolizin-4-one (S-22)

Melting point: 180°–182.5° C.
IR (KBr): 2220, 1700, 1680, 1625 cm$^{-1}$.
$^1$H NMR (CDCl$_3$): δ 0.88(t, 3H), 4.00(q, 2 H), 7.37–7.47(m, 3H), 7.54(brs, 1H), 7.62(m, 1H), 7.87(dt, 1H), 8.29(d, 1H), 9.42(d, 1H).

| Elementary analysis: $C_{19}H_{13}N_2O_3Br$ | | | |
|---|---|---|---|
| | C % | H % | N % |
| Calcd. | 57.45 | 3.30 | 7.05 |
| Found | 57.14 | 3.29 | 7.22 |

2-(3-Benzyloxy-4-methoxyphenyl)-3-cyano-1-ethoxycarbonyl-4H-quinolizin-4-one (S-23)

Melting point: 160°–160.5° C.
IR (KBr): 2210, 1705, 1680, 1625 cm$^{-1}$.
$^1$H NMR (CDCl$_3$): δ 0.82(t, 3H), 3.89(q, 2H), 3.94(s, 3H), 5.17(brs, 2 H), 6.97–7.07(m, 3H), 7.30–7.41(m, 4H), 7.46(d, 2 H), 7.80(dt, 1H), 8.15(d, 1H), 9.37(d, 1H).

| Elementary analysis: $C_{27}H_{22}N_2O_5$ | | | |
|---|---|---|---|
| | C % | H % | N % |
| Calcd. | 71.36 | 4.88 | 6.16 |
| Found | 71.30 | 4.79 | 6.21 |

2-(4-Benzyloxy-3-methoxyphenyl)-3-cyano-1-ethoxycarbonyl-4H-quinolizin-4-one (S-24)

Melting point: 170°–171.5° C.
IR (KBr): 2220, 1710, 1665, 1625 cm$^{-1}$.

¹H NMR (CDCl₃): δ 0.80(t, 3H), 3.91(s, 3H), 3.92(q, 2H), 5.21(brs, 2H), 6.90–7.00(m, 3H), 7.30–7.48(m, 6H), 7.80(dt, 1H), 8.14(d, 1H), 9.36(d, 1H).

| Elementary analysis: $C_{27}H_{22}N_2O_5$ | | | |
|---|---|---|---|
| | C % | H % | N % |
| Calcd. | 71.36 | 4.88 | 6.16 |
| Found | 71.72 | 4.89 | 6.32 |

3-Cyano-1-ethoxycarbonyl-2-(4-methylthiophenyl)-4H-quinolizin-4-one (S-25)

Melting point: 191°–193° C.
IR (KBr): 2205, 1700, 1665, 1620 cm⁻¹.
¹H NMR (CDCl₃): δ 0.85(t, 3 H), 2.54(s, 3H), 3.97(q, 2H), 7.34(brs, 4H), 7.37(t, 1H), 7.83(t, 1H), 8.21(d, 1H), 9.39(d, 1H).

| Elementary analysis: $C_{20}H_{16}N_2O_3S$ | | | |
|---|---|---|---|
| | C % | H % | N % |
| Calcd. | 65.92 | 4.43 | 7.69 |
| Found | 65.99 | 4.39 | 7.59 |

2-(4-Acetylaminophenyl)-3-cyano-1-ethoxycarbonyl-4H-quinolizin-4-one (S-26)

Melting point: 292°–296° C.
IR (KBr): 2215, 1720, 1700, 1650, 1620 cm⁻¹.
¹H NMR (DMSO-d₆): δ 1.36(t, 3H), 2.63(s, 3H), 4.50(q, 2H), 7.87(d, 2H), 8.17(m, 1H), 8.26(d, 2 H), 8.57–8.70(m, 2H), 9.81(d, 1H), 10.70(brs, 1H).

| Elementary analysis: $C_{21}H_{17}N_3O_4$ | | | |
|---|---|---|---|
| | C % | H % | N % |
| Calcd. | 67.19 | 4.56 | 11.19 |
| Found | 67.52 | 4.63 | 11.16 |

2-(4-Benzoylphenyl)-3-cyano-1-ethoxycarbonyl-4H-quinolizin-4-one (S-27)

Melting point: 226°–228° C.
IR (KBr): 2210, 1710, 1660, 1625 cm⁻¹.
¹H NMR (CDCl₃): δ 0.83(t, 3H), 3.98(q, 2H), 7.41–7.68(m, 6H), 7.82–7.98(m, 5H), 8.33(d, 1H), 9.44(d, 1H).

| Elementary analysis: $C_{26}H_{18}N_2O_4$ | | | |
|---|---|---|---|
| | C % | H % | N % |
| Calcd. | 73.92 | 4.29 | 6.63 |
| Found | 73.94 | 4.28 | 6.87 |

3-Cyano-2-(2,3-dimethoxyphenyl)-1-ethoxycarbonyl-4H-quinolizin-4-one (S-28)

Melting point: 147°–148° C.
IR (KBr): 2225, 1710, 1670, 1620 cm⁻¹.
¹H NMR (CDCl₃): δ 0.84(t, 3H), 3.86(s, 3H), 3.92(s, 3H), 3.99(q, 2H), 6.77(d, 1H), 7.04(d, 1H), 7.12(m, 1H), 7.39(t, 1H), 7.82(dt, 1H), 8.36(d, 1H), 9.41(d, 1H).

| Elementary analysis: $C_{21}H_{18}N_2O_5$ | | | |
|---|---|---|---|
| | C % | H % | N % |
| Calcd. | 66.66 | 4.79 | 7.40 |
| Found | 66.61 | 4.82 | 7.55 |

3-Cyano-2-(3,5-dimethoxyphenyl)-1-ethoxycarbonyl-4H-quinolizin-4-one (S-29)

Melting point: 175.5°–177° C.
IR (KBr): 2245, 1720, 1680, 1630 cm⁻¹.
¹H NMR (CDCl₃): δ 0.89(t, 3H), 3.81(brs, 6H), 4.02(q, 2H), 6.56(brs, 3H), 7.38(t, 1H), 7.84(dt, 1H), 8.20(d, 1H), 9.39(d, 1H).

| Elementary analysis: $C_{21}H_{18}N_2O_5$ | | | |
|---|---|---|---|
| | C % | H % | N % |
| Calcd. | 66.66 | 4.79 | 7.40 |
| Found | 66.71 | 4.94 | 7.34 |

EXAMPLE 3

3-Cyano-1-ethoxycarbonyl-2-(4-hydroxyphenyl)-4H-quinolizin-4-one (S-30)

A mixture of 165 mg of ethyl 2-pyridylacetate and 242 mg of 3-(4-acetoxyphenyl)-2-cyano-3-methoxyacrylonitrile was dissolved in 1 ml of dry N,N-dimethylformamide. To the solution was added 40 mg of 60% sodium hydride at room temperature and the reaction mixture was stirred for 1 hour at 60° C. The reaction mixture was poured into ice-water, and precipitated crystals were collected by filtration, washed with water and dried to obtain 120 mg of 2-(4-acetoxyphenyl)-3-cyano-1-ethoxycarbonyl-4-imino-4H-quinolizin. The obtained imine compound was added to 5 ml of 90% acetic acid and the reaction mixture was heated under reflux for 72 hours. After completion of the reaction, the solvent was evaporated under reduced pressure. The residue was dissolved in dichloromethane, and the solution was washed successively with 1N-hydrochloric acid, water and saturated sodium chloride solution and dried over anhydrous sodium sulfate. The solvent was evaporated and the residue was recrystallized from methanol to obtain 75 mg of 3-cyano-1-ethoxycarbonyl-2-(4-hydroxyphenyl)-4H-quinolizin-4-one.

Melting point: 284°–290° C.
IR (KBr): 3250, 2220, 1720, 1640, 1620 1610 cm⁻¹.
¹H NMR (DMSO-d₆): δ 0.97(t, 3H), 4.10(q, 2H), 7.02(d, 2 H), 7.34(d, 2H), 7.73(dt, 1H),, 8.15–8.25(m, 2H), 9.37(d, 1H), 10.02(brs, 1 H).

| Elementary analysis: $C_{19}H_{14}N_2O_4$ | | | |
|---|---|---|---|
| | C % | H % | N % |
| Calcd. | 68.26 | 4.22 | 8.38 |
| Found | 67.91 | 4.36 | 8.47 |

EXAMPLE 4

The following compounds were obtained according to the same procedure as described in Example 3.

3-Cyano-2-(3,4-dihydroxyphenyl)-1-ethoxycarbonyl-4H-quinolizin-4-one (S-31)

Melting point: 285°–287° C.
IR (KBr): 3400, 3250, 2220, 1720, 1665, 1625 cm⁻¹.

¹H NMR (DMSO-d₆): δ 1.00(t, 3H), 4.12(q, 2H), 6.88(dd, 1H), 6.90–7.11(m, 2H), 7.72(dt, 1H), 8.11–8.24(m, 2H), 9.36(d, 1H), 9.42(brs, 1H), 9.48(brs, 1H).

| Elementary analysis: C₁₉H₁₄N₂O₅ | | | |
|---|---|---|---|
| | C % | H % | N % |
| Calcd. | 65.14 | 4.03 | 8.00 |
| Found | 65.04 | 3.94 | 7.85 |

3-Cyano-1-ethoxycarbonyl-2-(4-hydroxy-3-methoxyphenyl)-4H-quinolizin-4-one (S-32)

Melting point: 190°–193° C.
IR (KBr): 3400, 2220, 1715, 1670, 1625 cm⁻¹.
¹H NMR (DMSO-d₆): δ 0.99(t, 3H), 3.89(s, 3H), 4.13(q, 2H), 6.93–7.10(m, 3H), 7.73(dt, 1H), 8.15–8.28(m, 2H), 9.37(d, 1H), 9.64(brs, 1H).

| Elementary analysis: C₂₀H₁₆N₂O₅ | | | |
|---|---|---|---|
| | C % | H % | N % |
| Calcd. | 65.93 | 4.43 | 7.69 |
| Found | 65.72 | 4.69 | 7.37 |

3-Cyano-1-ethoxycarbonyl-2-(3-hydroxy-4-methoxyphenyl)-4H-quinolizin-4-one (S-33)

Melting point: 220°–222° C.
IR (KBr): 3375, 2220, 1710, 1655, 1625 cm⁻¹.
¹H NMR (DMSO-d₆): δ 0.91(t, 3H), 3.96(s, 3H), 4.02(q, 2H), 5.68(brs, 1H), 6.91–7.02(m, 3H), 7.34(t, 1H), 7.79(dt, 1H), 8.14(d, 1H), 9.36(d, 1H).

| Elementary analysis: C₂₀H₁₆N₂O₅ | | | |
|---|---|---|---|
| | C % | H % | N % |
| Calcd. | 65.93 | 4.43 | 7.69 |
| Found | 65.71 | 4.39 | 7.67 |

EXAMPLE 5

2-(4-Aminophenyl)-3-cyano-1-ethoxycarbonyl-4H-quinolizin-4-one (S-34)

To a stirred solution of 100 mg of 3-cyano-1-ethoxycarbonyl-2-(4-nitrophenyl)-4H-quinolizin-4-one (S-20) in 10 ml of ethanol and 5 ml of acetone was added dropwise a solution of 240 mg of sodium hydrosulfite in 5ml of water during 10 minutes. The reaction mixture was heated under reflux for 1 hour and poured into ice-water. The solution was extracted with dichloromethane and the organic layer was dried over anhydrous sodium sulfate. The solvent was evaporated under reduced pressure and the residue was recrystallized from methanol to obtain 40 mg of 2-(4-aminophenyl)-3-cyano-1-ethoxycarbonyl-4H-quinolizin-4-one.
Melting point: 260°–262° C.
IR (KBr): 3450, 3350, 2210, 1720, 1660, 1630, 1605 cm⁻¹.
¹H NMR (DMSO-d₆): δ 1.03(t, 3H), 4.15(q, 2), 5.71(br, 2H), 6.78(d, 2H), 7.21(d, 2H), 7.67(dt, 1H), 8.06–8.19(m, 2H), 9.34(d, 1H).

| Elementary analysis: C₁₉H₁₅N₃O₃ | | | |
|---|---|---|---|
| | C % | H % | N % |
| Calcd. | 68.46 | 4.54 | 12.61 |
| Found | 67.88 | 4.46 | 12.16 |

REFERENCE EXAMPLE 1

3-Cyano-1-ethoxycarbonyl-2-methylthio-4H-quinolizin-4-one (R-1)

A mixture of 1.42 g of ethyl 2-pyridylacetate and 1.75 g of methyl 2-cyano-3,3-bismethylthioacrylate was heated at 120° C. for 10 hours. To the reaction mixture was added 8 ml of methanol, the precipitated crystals were collected by filtration and recrystallized from methanol to obtain 1.19 g of 3-cyano-1-ethoxycarbonyl-2-methylthio-4H-quinolizin-4-one as pale yellow crystals.
Melting point: 128°–129° C.
IR (KBr): 2200, 1695, 1665 cm⁻¹.
¹H NMR (CDCl₃): δ 1.44(t, 3H), 2.76(s, 3H), 4.48(q, 2H), 7.30(m, 1H), 7.80(m, 2H), 9.27(d, 1H).

| Elementary analysis: C₁₄H₁₂N₂O₃S | | | |
|---|---|---|---|
| | C % | H % | N % |
| Calcd. | 58.32 | 4.20 | 9.72 |
| Found | 57.79 | 4.22 | 9.82 |

REFERENCE EXAMPLE 2

The following compound was obtained according to the same procedure as described in Reference Example 1.

3-Cyano-2-methylthio-1-(3-phenylpropoxycarbonyl)-4H-quinolizin-4-one (R-2)

Melting point: 80°–81° C.
IR (KBr): 2200, 1700, 1665, 1620 cm⁻¹.
¹H NMR (CDCl₃): δ 2.13(m, 2H), 2.75(s, 3H), 2.78(t, 2H), 4.43(t, 2H), 7.18–7.36(m, 6H), 7.77(m, 2H), 9.26(d, 1H).

| Elementary analysis: C₂₁H₁₈N₂O₃S | | | |
|---|---|---|---|
| | C % | H % | N % |
| Calcd. | 66.65 | 4.79 | 7.40 |
| Found | 66.93 | 4.72 | 6.92 |

EXAMPLE 6

3-Cyano-1-ethoxycarbonyl-2-piperidino-4H-quinolizin-4-one (S-35)

A mixture of 1.44 g of 3-cyano-1-ethoxycarbonyl-2-methylthio-4H-quinolizin-4-one and 5.0 ml of piperidine in 10 ml of acetonitrile was heated under reflux for 10 hours. The reaction mixture was concentrated under reduced pressure and the residue was chromatographed on a silica gel column using a mixed solvent of ethyl acetate and n-hexane (2:1) as an eluent to obtain 0.95 g of 3-cyano-1-ethoxycarbonyl-2-piperidino-4H-quinolizin-4-one.
Melting point: 143°–144° C.
IR (KBr): 2200, 1710, 1665, 1630 cm⁻¹.

$^1$H NMR (CDCl$_3$): δ 1.38(t, 3H), 1.60–1.82(m, 6H), 3.33–6(m, 4H), 4.39(q, 2H), 6.99(t, 1H), 7.53(dt, 1H), 7.95(d, 1H), 9.06(d, 1H).

| Elementary analysis: C$_{18}$H$_{19}$N$_3$O$_3$ | | | |
|---|---|---|---|
| | C % | H % | N % |
| Calcd. | 66.45 | 5.89 | 12.91 |
| Found | 66.47 | 5.95 | 13.17 |

EXAMPLE 7

The following compounds were obtained according to the same procedure as described in Example 6.

3-Cyano-1-(3-phenylpropoxycarbonyl)-2-piperidino-4H-quinolizin-4-one (S-36)

Melting point: 97°–98° C.
IR (KBr): 2200, 1710, 1665, 1630 cm$^{-1}$.
$^1$H NMR (CDCl$_3$): δ 1.57–1.82(m, 6H), 2.09(m, 2H), 2.75(t, 2H), 3.42(m, 4H), 4.34(t, 2H), 7.00(t, 1H), 7.14–7.34(m, 5H), 7.53(dt, 1H), 7.93(d, 1H), 9.08(d, 1H).

| Elementary analysis: C$_{25}$H$_{25}$N$_3$O$_3$ | | | |
|---|---|---|---|
| | C % | H % | N % |
| Calcd. | 72.27 | 6.06 | 10.11 |
| Found | 72.37 | 6.19 | 10.35 |

3-Cyano-1-ethoxycarbonyl-2-(1-pyrrolidinyl)-4H-quinolizin-4one (S-37)

Melting point: 171°–172° C.
IR (KBr): 2200, 1700, 1650, 1620 cm$^{-1}$.
$^1$H NMR (CDCl$_3$): δ 1.40(t, 3H), 1.99(m, 4H), 3.81(m, 4H), 4.38(q, 2H), 6.82(t, 1H), 7.40(dt, 1H), 7.65(d, 1 H), 8.93(d, 1H).

| Elementary analysis: C$_{17}$H$_{17}$N$_3$O$_3$ | | | |
|---|---|---|---|
| | C % | H % | N % |
| Calcd. | 65.58 | 5.50 | 13.50 |
| Found | 65.56 | 5.62 | 13.66 |

3-Cyano-1-(3-phenylpropoxycarbonyl)-2-(1-pyrrolidinyl)-4H-quinolizin-4-one (S-38)

Melting point: 136°–137° C.
IR (KBr): 2210, 1695, 1650, 1620 cm$^{-1}$.
$^1$H NMR (CDCl$_3$): δ 1.97(m, 4H), 2.08(m, 2H), 2.74(t, 2H), 3.80(m, 4H), 4.32(t, 2H), 6.83(t, 1H), 7.16–7.43(m, 6H), 7.63(d, 1H), 8.93(d, 1H).

| Elementary analysis: C$_{24}$H$_{23}$N$_3$O$_3$ | | | |
|---|---|---|---|
| | C % | H % | N % |
| Calcd. | 71.80 | 5.77 | 10.47 |
| Found | 71.80 | 5.80 | 10.37 |

3-Cyano-1-ethoxycarbonyl-2-[4-(2-hydroxyethyl)-piperazin-1-yl]-4H-quinolizin-4-one (S-39)

Melting point: 159°–161° C.
IR (KBr): 2220, 1710, 1670, 1630 cm$^{-1}$.
$^1$H NMR (CDCl$_3$): δ 1.33(t, 3H), 1.75(br, 1H), 2.68(t, 2H), 2.77(br, 4H), 3.54(br, 4H), 3.68(t, 2H), 4.43(q, 2H), 7.06(t, 1H), 7.60(dt, 1H), 7.99(d, 1H), 9.12(d, 1H).

| Elementary analysis: C$_{19}$H$_{22}$N$_4$O$_4$ | | | |
|---|---|---|---|
| | C % | H % | N % |
| Calcd. | 61.61 | 5.99 | 15.13 |
| Found | 61.60 | 5.81 | 15.26 |

3-Cyano-1-ethoxycarbonyl-2-(4-formylpiperazin-1-yl)-4H-quinolizin-4-one (S-40)

Melting point: 235°–238° C.
IR (KBr): 2200, 1700, 1665, 1655, 1630 cm$^{-1}$.
$^1$H NMR (CDCl$_3$): δ 1.41(t, 3H), 3.37(t, 2H), 3.54(m, 2H), 3.65(m, 2H), 3.79(t, 2H), 4.43(q, 2H), 7.16(t, 1 H), 7.68(dt, 1H), 8.06(d, 1H), 8.15(brs, 1H), 9.18(d, 1H).

| Elementary analysis: C$_{18}$H$_{18}$N$_4$O$_4$ | | | |
|---|---|---|---|
| | C % | H % | N % |
| Calcd. | 61.01 | 5.12 | 15.81 |
| Found | 60.95 | 5.11 | 15.49 |

3-Cyano-2-(4-formylpiperazin-1-yl)-1-(3-phenylpropoxycarbonyl)-4H-quinolizin-4-one (S-41)

Melting point: 100°–104° C.
IR (KBr): 2210, 1705, 1665, 1630 cm$^{-1}$.
$^1$H NMR (CDCl$_3$): δ 2.09(m, 2H), 2.74(t, 2H), 3.35(t, 2H), 3.50(m, 2H), 3.61(m, 2H), 3.75(m, 2H), 4.36(t, 2H), 7.13–7.32(m, 6H), 7.69(dt, 1H), 8.00(d, 1H), 8.13(brs, 1H), 9.19(d, 1H).

| Elementary analysis: C$_{25}$H$_{24}$N$_4$O$_4$ | | | |
|---|---|---|---|
| | C % | H % | N % |
| Calcd. | 67.56 | 5.44 | 12.60 |
| Found | 67.51 | 5.40 | 12.44 |

3-Cyano-1-ethoxycarbonyl-2-(4-methylpiperazin-1-yl)-4H-quinolizin-4-one (S-42)

Melting point: 187°–188° C.
IR (KBr): 2210, 1710, 1660, 1630 cm$^{-1}$.
$^1$H NMR (CDCl$_3$): δ 1.40(t, 3H), 2.39(brs, 3H), 2.65(br, 4H), 3.54(br, 4H), 4.40(q, 2H), 7.05(t, 1H), 7.59(dt, 1H), 8.00(d, 1H), 9.11(d, 1H).

| Elementary analysis C$_{18}$H$_{20}$N$_4$O$_3$ | | | |
|---|---|---|---|
| | C % | H % | N % |
| Calcd. | 63.52 | 5.92 | 16.46 |
| Found | 63.44 | 6.09 | 16.60 |

3-Cyano-2-(4-methylpiperazin-1-yl)-1-(3-phenylpropoxycarbonyl)-4H-quinolizin-4-one (S-43)

Melting point: 118°–120° C.
IR (KBr): 2210, 1710, 1670, 1630 cm$^{-1}$.
$^1$H NMR (CDCl$_3$): δ 2.10(m, 2H), 2.39(brs, 3H), 2.67(br, 4H), 2.73(t, 2H), 3.54(br, 4H), 4.37(t, 2H), 7.07(t, 1H), 7.13–7.30(m, 5H), 7.59(dt, 1H), 7.98(d, 1H), 9.12(d, 1H).

| Elementary analysis: C$_{25}$H$_{26}$N$_4$O$_3$ | | | |
|---|---|---|---|
| | C % | H % | N % |
| Calcd. | 69.75 | 6.09 | 13.01 |

| Elementary analysis: C$_{25}$H$_{26}$N$_4$O$_3$ | | | |
|---|---|---|---|
| | C % | H % | N % |
| Found | 69.85 | 6.01 | 12.77 |

2-(4-Benzylpiperidino)-3-cyano-1-ethoxycarbonyl-4H-quinolizin-4-one (S-44)

Melting point: 168°–170° C.
IR (KBr): 2205, 1705, 1665, 1625 cm$^{-1}$.
$^1$H NMR (CDCl$_3$): δ 1.38(t, 3H), 1.47–1.82(m, 5H), 2.62(d, 2H), 3.02(t, 2H), 3.80(d, 2H), 4.37(q, 2H), 6.9(t, 1H), 7.14–7.33(m, 5H), 7.54(dt, 1 H), 7.95(d, 1H), 9.08(d, 1H).

| Elementary analysis: C$_{25}$H$_{25}$N$_3$O$_3$ | | | |
|---|---|---|---|
| | C % | H % | N % |
| Calcd. | 72.27 | 6.06 | 10.11 |
| Found | 72.45 | 6.11 | 10.01 |

2-(4-Benzylpiperidino)-3-cyano-1-(3-phenylpropoxycarbonyl)-4H-quinolizin-4-one (S-45)

Melting point: 169°–171° C.
IR (KBr): 2210, 1705, 1670, 1630 cm$^{-1}$.
$^1$H NMR (CDCl$_3$): δ 1.45–1.80(m, 5H), 2.07(m, 2H), 2.60(d, 2H), 2.73(t, 2H), 3.03(t, 2H), 3.79(d, 2H), 4.31(t, 2H), 7.01(t, 1H), 7.12–7.33(m, 10H), 7.55(dt, 1H), 7.91(d, 1H), 9.10(d, 1H).

| Elementary analysis: C$_{32}$H$_{31}$N$_3$O$_3$ | | | |
|---|---|---|---|
| | C % | H % | N % |
| Calcd. | 76.02 | 6.18 | 8.31 |
| Found | 75.85 | 6.18 | 8.08 |

3-Cyano-1-ethoxycarbonyl-2-(4-phenylpiperidino)-4H-quinolizin-4-one (S-46)

Melting point: 162°–164° C.
IR (KBr): 2210, 1700, 1670, 1630 cm$^{-1}$.
$^1$H NMR (CDCl$_3$): δ 1.46(t, 3H), 1.90–2.11(m, 4H), 2.87(m, 1H), 3.25(dt, 2H), 3.94(d, 2H), 4.44(q, 2H), 7.03(t, 1H), 7.19–7.38(m, 5H), 7.58(d, 1H), 7.98(d, 1H), 9.11(d, 1H).

| Elementary analysis: C$_{24}$H$_{23}$N$_3$O$_3$ | | | |
|---|---|---|---|
| | C % | H % | N % |
| Calcd. | 71.80 | 5.77 | 10.47 |
| Found | 71.51 | 5.76 | 10.18 |

3-Cyano-2-(4-phenylpiperidino)-1-(3-phenylpropoxycarbonyl)-4H-quinolizin-4-one (S-47)

Amorphous solid
IR (KBr): 2210, 1710, 1665, 1630 cm$^{-1}$.
$^1$H NMR (CDCl$_3$): δ 1.91–2.19(m, 6H), 2.69–2.82(m, 3H), 3.23(dt, 2H), 3.93(d, 2H), 4.39(t, 2H), 7.05(t, 1H), 7.17–7.38(m, 10H), 7.69(dt, 1H), 7.96(d, 1H), 9.13(d, 1H).

| Elementary analysis: C$_{31}$H$_{29}$N$_3$O$_3$ | | | |
|---|---|---|---|
| | C % | H % | N % |
| Calcd. | 75.74 | 5.95 | 8.55 |
| Found | 75.91 | 5.88 | 8.40 |

3-Cyano-1-ethoxycarbonyl-2-morpholino-4H-quinolizin-4-one (S-48)

Melting point: 205°–206° C.
IR (KBr): 2220, 1710, 1660, 1625 cm$^{-1}$.
$^1$H NMR (CDCl$_3$): δ 1.43(t, 3H), 3.49(t, 4H), 3.88(t, 4H), 4.43(q, 2H), 7.08(t, 1H), 7.63(dt, 1H), 8.00(d, 1H), 9.14(d, 1H).

| Elementary analysis: C$_{17}$H$_{17}$N$_3$O$_4$ | | | |
|---|---|---|---|
| | C % | H % | N % |
| Calcd. | 62.38 | 5.23 | 12.84 |
| Found | 62.10 | 5.17 | 12.89 |

3-Cyano-2-morpholino-1-(3-phenylpropoxycarbonyl)-4H-quinolizin-4-one (S-49)

Melting point: 112°–113° C.
IR (KBr): 2225, 1705, 1670, 1630 cm$^{-1}$.
$^1$H NMR (CDCl$_3$): δ 2.11(m, 2H), 2.75(t, 2H), 3.48(t, 4H), 3.88(t, 4H), 4.39(t, 2H), 7.09(t, 1H), 7.15–7.33(m, 5H), 7.61(dt, 1H), 7.96(d, 1H), 9.15(d, 1H).

| Elementary analysis: C$_{24}$H$_{23}$N$_3$O$_4$ | | | |
|---|---|---|---|
| | C % | H % | N % |
| Calcd. | 69.05 | 5.55 | 10.07 |
| Found | 69.45 | 5.68 | 10.27 |

3-Cyano-1-ethoxycarbonyl-2-(imidazol-1-yl)-4H-quinolizin-4-one (S-50)

Melting point: 141°–142° C.
IR (KBr): 2230, 1715, 1685, 1620 cm$^{-1}$.
$^1$H NMR (CDCl$_3$): δ 1.06(t, 3H), 4.09(q, 2H), 7.27(brs, 1H), 7.29(brs, 1H), 7.54(t, 1H), 7.79(brs, 1H), 8.00(dt, 1H), 8.43(d, 1H), 9.46(d, 1H).

| Elementary analysis: C$_{16}$H$_{12}$N$_4$O$_3$ | | | |
|---|---|---|---|
| | C % | H % | N % |
| Calcd. | 62.33 | 3.92 | 18.17 |
| Found | 62.41 | 3.92 | 18.11 |

3-Cyano-2-(imidazol-1-yl)-1-(3-phenylpropoxycarbonyl)-4H-quinolizin-4-one (S-51)

Melting point: 123°–129° C.
IR (KBr): 2220, 1720, 1680, 1620 cm$^{-1}$.
$^1$H NMR (CDCl$_3$): δ 1.20(m, 2H), 2.50(t, 2H), 4.06(t, 2H), 7.07–7.30(m, 7H), 7.55(t, 1H), 7.80(brs, 1H), 8.00(dt, 1H), 8.40(d, 1H), 9.46(d, 1H).

| Elementary analysis: C$_{23}$H$_{18}$N$_4$O$_3$ | | | |
|---|---|---|---|
| | C % | H % | N % |
| Calcd. | 69.34 | 4.55 | 14.06 |
| Found | 69.30 | 4.56 | 14.21 |

3-Cyano-1-ethoxycarbonyl-2-(1,3,4-triazol-1-yl)-4H-quinolizin-4-one (S-52)

Melting point: 164.5°–165.5° C.
IR (KBr): 2220, 1715, 1690, 1620 cm$^{-1}$.
$^1$H NMR (CDCl$_3$): δ 1.05(t, 3H), 4.13(q, 2H), 7.55(t, 1H), 8.00(t, 1H), 8.20(s, 1H), 8.50(d, 1H), 8.76(s, 1H), 9.47(d, 1H).

| Elementary analysis: C$_{15}$H$_{11}$N$_5$O$_3$ | | | |
|---|---|---|---|
| | C % | H % | N % |
| Calcd. | 58.25 | 3.58 | 22.64 |
| Found | 58.22 | 3.65 | 22.31 |

3-Cyano-1-(3-phenylpropoxycarbonyl)-2-(1,3,4-triazol-1-yl)-4H-quinolizin-4-one (S-53)

Melting point: 159°–160° C.
IR (KBr): 2210, 1720, 1680, 1620 cm$^{-1}$.
$^1$H NMR (CDCl$_3$): δ 1.74(m, 2H), 2.52(t, 2H), 4.10(t, 2H), 7.07–7.31(m, 5H), 7.54(t, 1H), 8.00(dt, 1H), 8.16(s, 1H), 8.46(d, 1H), 8.76(s, 1H), 9.47(d, 1H).

| Elementary analysis: C$_{22}$H$_{17}$N$_5$O$_3$ | | | |
|---|---|---|---|
| | C % | H % | N % |
| Calcd. | 66.16 | 4.29 | 17.53 |
| Found | 65.63 | 4.31 | 17.26 |

3-Cyano-2-[4-(2-hydroxyethyl)piperazin-1-yl]-1-(3-phenylpropoxycarbonyl)-4H-quinolizin-4-one (S-54)

Melting point: 138°–141° C.
IR (KBr): 2210, 1710, 1675, 1625 cm$^{-1}$.
$^1$H NMR (CDCl$_3$): δ 1.62(br, 1H), 2.12(m, 2H), 2.64–2.81(m, 8H), 3.55(br, 4H), 3.79(br, 2H), 4.39(t, 2H), 7.08(t, 1H), 7.17–7.32(m, 5H), 7.62(dt, 1H), 7.97(d, 1H), 9.13(d, 1H).

| Elementary analysis: C$_{26}$H$_{28}$N$_4$O$_4$ | | | |
|---|---|---|---|
| | C % | H % | N % |
| Calcd. | 67.81 | 6.13 | 12.17 |
| Found | 67.80 | 6.15 | 12.03 |

3-Cyano-1-ethoxycarbonyl-2-(4-morpholinocarbonylmethylpiperazin-1-yl)-4H-quinolizin-4-one (S-55)

Melting point: 178°–179° C.
IR (KBr): 2210, 1695, 1670, 1625 cm$^{-1}$.
$^1$H NMR (CDCl$_3$): δ 1.43(t, 3H), 2.70–3.76(m, 18H), 4.46(q, 2H), 7.10(t, 1H), 7.74(t, 1H), 8.04(d, 1H), 9.15(d, 1H).

| Elementary analysis: C$_{23}$H$_{27}$N$_5$O$_5$ | | | |
|---|---|---|---|
| | C % | H % | N % |
| Calcd. | 60.92 | 6.00 | 15.44 |
| Found | 60.53 | 6.07 | 14.98 |

3-Cyano-2-(4-morpholinocarbonylmethylpiperazin-1-yl)-1-(3-phenylpropoxycarbonyl)-4H-quinolizin-4-one (S-56)

Melting point: 198°–200° C.
IR (KBr): 2210, 1695, 1675, 1525 cm$^{-1}$.
$^1$H NMR (CDCl$_3$): δ 2.11(m, 2H), 2.75(t, 2H), 3.25–3.73(m, 18H), 4.41(t, 2H), 7.09(t, 1H), 7.14–7.31(m, 5H), 7.62(t, 1H), 8.08(d, 1H), 9.14(d, 1H).

| Elementary analysis: C$_{30}$H$_{33}$N$_5$O$_5$ | | | |
|---|---|---|---|
| | C % | H % | N % |
| Calcd. | 66.28 | 6.12 | 12.88 |
| Found | 66.38 | 6.09 | 12.89 |

EXAMPLE 8

3-Cyano-1-(2-hydroxyethyloxycarbonyl)-2-piperidino-4H-quinolizin-4-one (S-57)

To a solution of 1.10 g of 3-cyano-1-ethoxycarbonyl-2-piperidino-4H-quinolizin-4-one (Example 6, S-35) in 30 ml of ethylene glycol was added 150 mg of 60% sodium hydride, and the reaction mixture was stirred at 100° C. for 14 hours. After cooling, the precipitated crystals were collected by filtration and then the crude crystals were chromatographed on a silica gel column using a mixed solvent of dichloromethane and diethyl ether (1:1) as an eluent to obtain 180 mg of 3-cyano-1-(2-hydroxyethoxycarbonyl)-2-piperidino-4H-quinolizin-4-one.

Melting point: 140°–141° C.
IR (KBr): 3375, 2210, 1710, 1675, 1640, 1630 cm$^{-1}$.
$^1$H NMR (CDCl$_3$): δ 1.62–1.82(m, 7H), 3.47(m, 4H), 3.99(m, 2H), 4.47(m, 2H), 7.00(t, 1H), 7.55(dt, 1H), 8.02(d, 1H), 9.07(d, 1H).

| Elementary analysis: C$_{18}$H$_{19}$N$_3$O$_4$ | | | |
|---|---|---|---|
| | C % | H % | N % |
| Calcd. | 63.33 | 5.61 | 12.31 |
| Found | 63.01 | 5.59 | 12.19 |

TEST EXAMPLE

Determination of Igs Produced in In Vitro Culture

BALB/c mice were immunized intraperitoneally with 5 μg of DNP-As adsorbed on 4 mg aluminum hydroxide gel. Four weeks after the immunization, the spleens were excised from the mice and 5×10$^7$ spleen cells were transferred intravenously into the recipient mice which had been exposed to 600 rad of X-ray irradiation. Immediately after cell transfer, the recipients were then immunized intraperitoneally with 5 μg of DNP-As adsorbed on 4 mg aluminum hydroxide gel to induce adoptive secondary immune response. Further 4 weeks after the immunization of recipients, the spleens were excised from then and the spleen cell suspensions containing 5×10$^6$ cells/ml were cultured with or without a compound to be tested in 96-well micro-titer plates at 37° C. for 4 days. IgE and IgG secreted into the culture supernatant was each determined correspondingly by ELISA and the inhibitory effect was calculated according to the following equation.

$$\text{inhibition \%} = \frac{\text{average amount of } Ig \text{ in control group} - \text{average amount of } Ig \text{ in test group}}{\text{average amount of } Ig \text{ in control group}} \times 100$$

The results obtained were shown below:

| Comp. No. | Concentration (μg/ml) | Inhibition % of IgE | Inhibition % of IgG |
|---|---|---|---|
| S- 1 | 5 | 47 | 1 |
| S- 3 | 49 | 34 | 15 |
| S- 6 | 10 | 65 | 37 |
| S- 8 | 40 | 51 | 5 |
| S- 9 | 5 | 64 | 32 |
| S- 10 | 10 | 57 | 22 |
| S- 11 | 40 | 46 | 19 |
| S- 12 | 20 | 50 | 8 |
| S- 13 | 40 | 64 | 26 |
| S- 19 | 20 | 48 | 8 |
| S- 20 | 10 | 49 | 9 |
| S- 25 | 20 | 61 | −4 |
| S- 28 | 2.5 | 64 | 14 |
| S- 29 | 40 | 67 | 17 |
| S- 30 | 40 | 43 | −20 |
| S- 31 | 20 | 54 | −7 |
| S- 32 | 20 | 53 | −9 |
| S- 33 | 40 | 58 | 5 |
| S- 35 | 5 | 30 | 17 |
| S- 36 | 5 | 39 | −4 |
| S- 38 | 1 | 68 | 1 |
| S- 39 | 40 | 63 | 17 |
| S- 40 | 40 | 34 | 9 |
| S- 41 | 2.5 | 75 | 9 |
| S- 42 | 40 | 63 | 19 |
| S- 43 | 2.5 | 65 | 1 |
| S- 45 | 1 | 55 | 16 |
| S- 49 | 2.5 | 61 | 21 |
| S- 54 | 5 | 59 | 4 |
| S- 55 | 40 | 36 | −4 |
| S- 56 | 2.5 | 37 | 1 |

What is claimed is:

1. A method for the treatment of allergic bronchial asthma, allergic rhinitis, atopic dermatitis and hypersensitiveness diseases associated with immunoglobulin E-antibody formation in a mammal which comprises administering an effective dosage from about 0.1 mg to 10 mg per kg of mammal weight by oral administration of from about 0.02 mg to 5 mg per kg of mammal weight by parenteral administration per day of an immunoglobulin E-antibody formation-inhibiting 4H-quinolizin-4-one compound to the mammal; wherein the 4H-quinolizin-4-one compound corresponds to the formula:

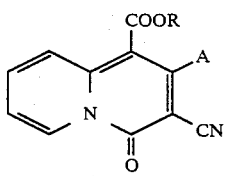

where R is an alkyl group or a phenylalkyl group; A is a substituted or unsubstituted phenyl group or a substituted or unsubstituted 5 or 6 membered heterocyclic group; with the proviso that the heterocyclic group is bonded to the quinolizine ring at a nitrogen atom of the heterocyclic ring; or a pharmaceutically acceptable salt thereof.

2. A method for the treatment of allergic bronchial asthma, allergic rhinitis, atopic dermatitis and hypersensitiveness diseases associated with immunoglobulin E-antibody formation in a mammal which comprises administering an effective dosage from about 0.1 mg to 10 mg per kg of mammal weight by oral administration or from about 0.02 mg to 5 per kg of mammal weight by parenteral administration per day of an immunoglobulin E-antibody formation-inhibiting 4H-quinolizin-4-one compound to the mammal; wherein the 4H-quinolizin-4-one compound corresponds to the formula:

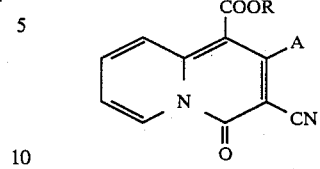

where R is an alkyl group or a phenylalkyl group; Ar is a substituted or unsubstituted phenyl group; or a pharmaceutically acceptable salt thereof.

3. A method for the treatment of allergic bronchial asthma, allergic rhinitis, atopic dermatitis and hypersensitiveness diseases associated with immunoglobulin E-antibody formation in a mammal which comprises administering an effective dosage from about 0.1 mg to 10 mg per kg of mammal weight by oral administration or from about 0.02 mg to 5 mg per kg mammal weight by parenteral administration per day of an immunoglobulin E-antibody formation-inhibiting 4H-quinolizin-4-one compound to the mammal; wherein the 4H-quinolizin-4-one compound corresponds to the formula:

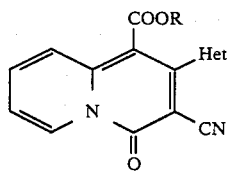

where R is an alkyl group or a phenylalkyl group; Het is a 5 or 6 membered heterocyclic group; with the proviso that the heterocyclic group is bonded to the quinolizine ring at a nitrogen atom of the heterocyclic ring; or a pharmaceutically acceptable salt thereof.

4. A method for the treatment of allergic bronchial asthma, allergic rhinitis, atopic dermatitis and hypersensitiveness diseases associated with immunoglobulin E-antibody formation in a mammal which comprises administering an effective dosage from about 0.1 mg to 10 mg per kg of mammal weight by oral administration or from about 0.02 mg to 5 mg per kg of mammal weight by parenteral administration per day of an immunoglobulin E-antibody formation-inhibiting 4H-quinolizin-4-one compound to the mammal; wherein the 4H-quinolizin-4-one compound is selected from the group consisting of 3-cyano-1-ethoxycarbonyl-2-phenyl-4H-quinolizin- 4-one; 2-(4-biphenylyl)-3-cyano-1-ethoxycarbonyl-4H-quinolizin-4-one; 2-(4-Bromophenyl)-3-cyano-1-ethoxycarbonyl-4H-quinolizin-4-one; 3-cyano-1-ethoxycarbonyl-2-(4-tertbutylphenyl)-4H-quinolizin-4-one; 3-cyano-2-(3,4-dimethoxyphenyl)-1-ethoxycarbonyl-4H-quinolizin-4-one; 3-cyano-1-ethoxycarbonyl-2-(4-methoxyphenyl)-4H-quinolizin-4-one; 3-cyano-1-ethoxycarbonyl-2-(4-methylphenyl)-4H-quinolizin-4-one; 3-cyano-1-ethoxycarbonyl-2-(3,4-methylenedioxyphenyl)-4H-quinolizin-4-one; 3-cyano-2-(2,4-dichlorophenyl)-1-ethoxycarbonyl-4H-quinolizin-4-one; 3-cyano-2-phenyl-1-propoxycarbonyl-4H-quinolizin-4-one; 3-cyano-1-methoxycarbonyl-2-phenyl-4H-quinolizin-4-one; 3-cyano-1-ethoxycarbonyl-2-(4-fluorophenyl)-4H-quinolizin-4-one; 3-cyano-1-ethoxycarbonyl-2-(3-fluoro-4-methylphenyl)-4H-quinolizin-4-one; 3-cyano-2-(3,4-dimethylphenyl)-1-ethoxycarbonyl-4H-quinolizin-4-one; 3-cyano-1-ethoxycarbonyl-2-(4-ethoxyphenyl)-4H-quinolizin-4-one; 3-cyano-1-ethoxycarbonyl-2-(4-isopropoxyphenyl)-4H-quinolizin-4-one; 3-cyano-1-ethoxycarbonyl-2-(3-methoxyphenyl)-4H-quinolizin-4-one; 2-(4-benzyloxyphenyl)-3-cyano-1-ethoxycarbonyl-4H-quinolizin-4-one; 3-cyano-1-ethoxycarbonyl-2-(3,4,5-trimethoxyphenyl)-4H-quinolizin-4-one; 3-cyano-1-ethoxycarbonyl-2-(4-nitrophenyl)-4H-quinolizin-4-one; 3-cyano-1-ethoxycarbonyl-2-(2-methoxyphenyl)-4H-quinolizin-4-one; 2-(3-bromophenyl)-3-cyano-1-ethoxycarbonyl-4H-quinolizin4-one; 2-(3-benzyloxy-4-methoxyphenyl)-3-cyano-1-ethoxycarbonyl-4H-quinolizin-4-one; 2-(4-benzyloxy-3-methoxyphenyl)-3-cyano-1-ethoxycarbonyl-4H-quinolizin-4-one; 3-cyano-1-ethoxycarbonyl-2-(4-methylthiophenyl)-4H-quinolizin-4-one; 2(4-acetylaminophenyl)-3-cyano-1-ethoxycarbonyl-4H-quinolizin-4-one; 2-(4-benzoylphenyl)-3-cyano-1-ethoxycarbonyl-4H-quinolizin-4-one; 3-cyano-2-(2,3-dimethoxyphenyl)-1-ethoxycarbonyl-4H-quinolizin-4-one; 3-cyano-2-(3,5-dimethoxyphenyl)-1-ethoxycarbonyl-4H-quinolizin-4-one; 3-cyano-1-ethoxycarbonyl-2-(4-hydroxyphenyl)-4H-quinolizin-4-one; 3-cyano-2-(3,4-dihydroxyphenyl)-1-ethoxycarbonyl-4H-quinolizin-4-one; 3-cyano-1-ethoxycarbonyl-2-(4-hydroxy-3-methoxyphenyl)-4H-quinolizin-4-one; 3-cyano-1-ethoxycarbonyl-2-(3-hydroxy-4-methoxyphenyl)-4H-quinolizin-4-one; 2-(4-aminophenyl)-3-cyano-1-ethoxycarbonyl-4H-quinolizin-4-one; 3-cyano-1-ethoxycarbonyl-2-methylthio-4H-quinolizin-4-one; 3-cyano-2-methylthio-1-(3-phenylpropoxycarbonyl)-4H-quinolizin-4-one; 3-cyano-1-ethoxycarbonyl-2-piperidino-4H-quinolizin-4-one; 3-cyano-1-(3-phenylpropoxycarbonyl)-2-piperidino-4H-quinolizin-4-one; 3-cyano-1-ethoxycarbonyl-2-(1-pyrrolidinyl)-4H-quinolizin-4-one; 3-cyano-1-(3-phenylpropoxycarbonyl)-2-(1-pyrrolidinyl)-4Hquinolizin-4-one; 3-cyano-1-ethoxycarbonyl-2-[4-(2-hydroxyethyl)piperazin-1-yl-4H-quinolizin-4-one; 3-cyano-1-ethoxycarbonyl-2-(4-formylpiperazin-1-yl)-4H-quinolizin-4-one; 3-cyano-2-(4-formylpiperazin-1-yl)-1-(3-phenylpropoxycarbonyl)-4H-quinolizin-4-one; 3-cyano-1-ethoxycarbonyl-2-(4-methylpiperazin-1-yl)-4H-quinolizin-4one; 3-cyano-2-(4-methylpiperazin-1-yl)-1-(3-phenylpropoxycarbonyl)-4H-quinolizin-4-one; 2-(4-benzylpiperidino)-3-cyano-1-ethoxycarbonyl-4H-quinolizin-4-one; 2-(4-benzylpiperidino)-3-cyano-1-(3-phenylpropoxycarbonyl)-4H-quinolizin-4-one; 3-cyano-1-ethoxycarbonyl-2-(4-phenylpiperidino)-4H-quinolizin-4-one; 3-cyano-2-(4-phenylpiperidino)-1-(3-phenylpropoxycarbonyl)-4H-quinolizin-4-one; 3-cyano-1-ethoxycarbonyl-2-morpholino-4H-quinolizin-4-one; 3-cyano-2-morpholino-1-(3-phenylpropoxycarbonyl)-4H-quinolizin-4-one; 3-cyano-1-ethoxycarbonyl-2-(imidazol-1-yl)-4H-quinolizin-4-one; 3-cyano-2-(imidazol-1-yl)-1-(3-phenylpropoxycarbonyl)-4H-quinolizin-4-one; 3-cyano-1-ethoxycarbonyl-2-(1,3,4-triazol-1-yl)-4H-quinolizin-4-one; 3-cyano-1-(3-phenylpropoxycarbonyl)-2-(1,3,4-triazol-1-yl)-4H-quinolizin-4-one; 3-cyano-2-[4-(2-hydroxyethyl)piperazin-1-yl]-1-(3-phenylpropoxycarbonyl)-4H-quinolizin-4-one; 3-cyano-1-ethoxycarbonyl-2-(4-morpholinocarbonylmethylpiperazin-1-yl)-4H-quinolizin-4-one; 3-cyano-2-4-morpholinocarbonylmethylpiperazin-1-yl)-1-(3-phenylpropoxycarbonyl)-4H-quinolizin-4-one; and 3-cyano-1-(2-hydroxyethyloxycarbonyl)-2-piperidino-4H-quinolizin-4-one;or a pharmaceutically acceptable salt thereof.

* * * * *

UNITED STATES PATENT AND TRADEMARK OFFICE
CERTIFICATE OF CORRECTION

PATENT NO. : 4,904,657
DATED : February 27, 1990
INVENTOR(S) : Kurashina et al

It is certified that error appears in the above-identified patent and that said Letters Patent is hereby corrected as shown below:

Col. 2, line 64, "829710" should be --8429710--.

Col. 3, line 24, "form" should be --from--.

Col. 6, line 37, "are previously" should be --are as previously--.

Col. 19, line 33 (Title), "4one" should be --4-one--.

Col. 24, line 56, "from then" should be --from them--.

Col. 26, line 6 (Formula), "A" should be --Ar--.

Col. 27, line 11, "quinolizin4" should be --quinolizin-4--.

Signed and Sealed this

Third Day of December, 1991

Attest:

HARRY F. MANBECK, JR.

*Attesting Officer*     *Commissioner of Patents and Trademarks*